United States Patent [19]

McLeod et al.

[11] Patent Number: 5,273,028
[45] Date of Patent: Dec. 28, 1993

[54] NON-INVASIVE MEANS FOR IN-VIVO BONE-GROWTH STIMULATION

[76] Inventors: Kenneth J. McLeod, 28 Setalcott Pl., Setauket, N.Y. 11733; Clinton T. Rubin, 108 Bleeker St., Port Jefferson, N.Y. 11776

[21] Appl. No.: 51,462

[22] Filed: May 18, 1993

Related U.S. Application Data

[63] Continuation-in-part of Ser. No. 891,151, May 29, 1992, abandoned, which is a continuation-in-part of Ser. No. 865,148, Apr. 13, 1992, Pat. No. 5,191,880, which is a continuation of Ser. No. 560,186, Jul. 31, 1990, Pat. No. 5,103,806.

[51] Int. Cl.$^5$ .............................................. A61H 1/00
[52] U.S. Cl. ............................................................. 128/33
[58] Field of Search .......................................... 128/25

[56] References Cited

U.S. PATENT DOCUMENTS

| | | | |
|---|---|---|---|
| 4,710,655 | 12/1987 | Masaki | 128/41 |
| 4,782,822 | 11/1988 | Ricken | 128/33 |
| 4,858,599 | 8/1989 | Halpern | 128/33 |
| 4,873,966 | 10/1989 | Gitter | 128/33 |
| 5,046,484 | 9/1991 | Bassett et al. | 128/25 R |

*Primary Examiner*—Ruth S. Smith
*Attorney, Agent, or Firm*—Hopgood, Calimafde, Kalil, Blaustein & Judlowe

[57] ABSTRACT

A method and apparatus for preventing osteopenia, promoting bone tissue growth, ingrowth, and healing of bone tissue includes the step of and apparatus for applying a mechanical load to the bone tissue at a relatively low level on the order of between about 50 and about 500 microstrain peak-to-peak, and at a relatively high frequency, preferably in the range of about 15 and about 55 Hz. Mechanical loading at such strain levels and such frequencies has been found to prevent bone loss and enhance new bone formation.

54 Claims, 2 Drawing Sheets

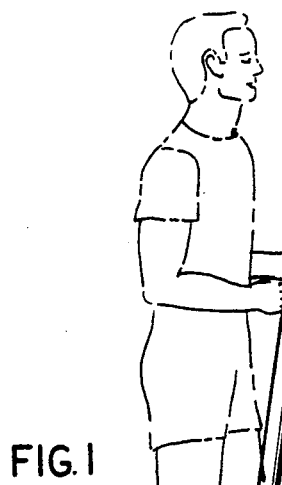
FIG.1
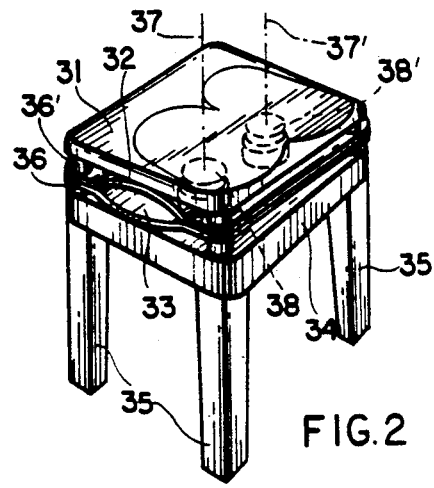
FIG.2
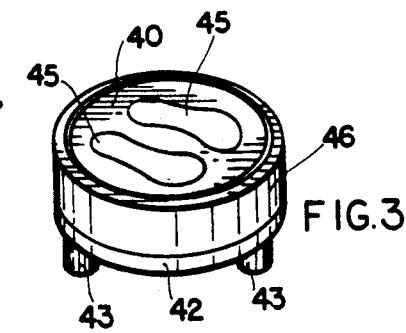
FIG.3
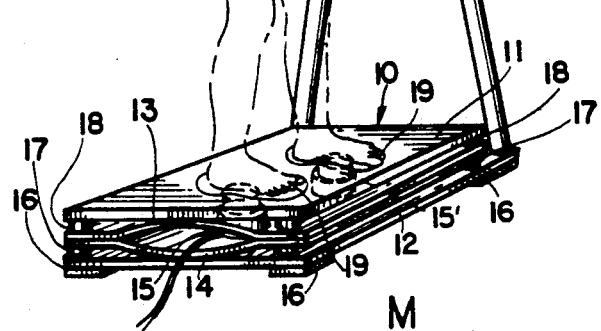
FIG.4
FIG.4A
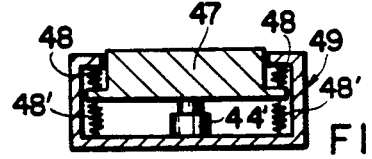
FIG.5
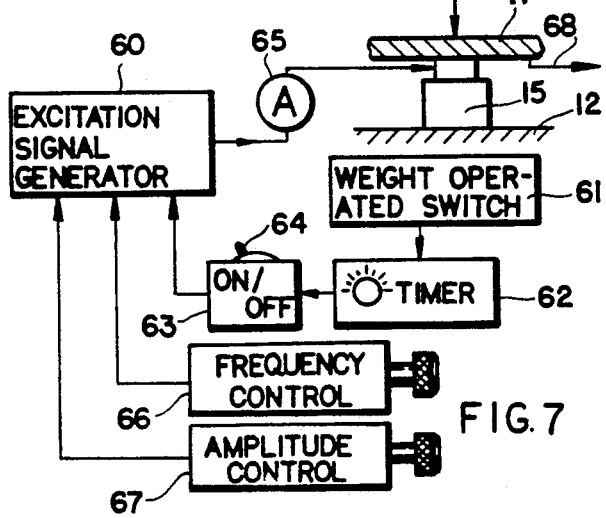
FIG.7
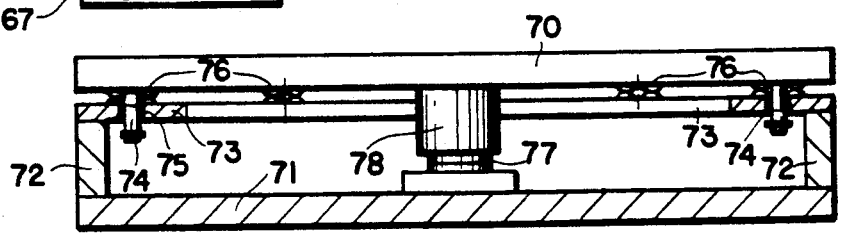
FIG.6

NON-INVASIVE MEANS FOR IN-VIVO BONE-GROWTH STIMULATION

RELATED CASES

This application is a continuation-in-part of our copending application Ser. No. 07/891,151, filed May 29, 1992 now abandoned; said copending application Ser. No. 07/891,151 is a continuation-in-part of our then-pending application Ser. No. 07/865,148, filed Apr. 13, 1992 (now U.S. Pat. No. 5,191,880), and said then-pending application is a continuation of our original application, Ser. No. 07/560,186, filed Jul. 31, 1990 (now U.S. Pat. No. 5,103,806).

BACKGROUND OF THE INVENTION

This invention generally relates to a method and means for inducing mechanical strain in bone tissue, and more specifically relates to a non-invasive method and means for preventing osteopenia, and promoting growth, ingrowth and healing of bone tissue by mechanically loading the bone tissue.

DESCRIPTION OF THE PRIOR ART

Numerous publications and patents disclose various methods of maintaining or promoting bone-tissue growth. For example, Ryaby, et al. U.S. Pat. Nos. 4,105,017, 4,266,532, 4,266,533 and 4,315,503 collectively describe means and methods for inducing voltage and current signals in bone tissue for the treatment or repair of bone fractures. Kraus, et al. U.S. Pat. No. 3,890,953 discloses stimulating the healing of fractures by the application of magnetic fields, the effect of which is described as introducing mechanical stress.

U.S. Pat. No. 4,530,360 which issued to Luiz Duarte discloses a method for healing bone fractures by the application of ultrasound. Also, the piezoelectric response of mechanically stressed bone is disclosed in the article, *Generation of Electric Potentials by Bone in Response to Mechanical Stress*, published in Science Magazine 137, 1063–1064, Sep. 28, 1962.

Many conventional methods of promoting bone-tissue growth and bone maintenance by the application of mechanical loads generally tend to apply relatively low frequency or low repetition rate (e.g., less than 5 Hz), relatively high magnitude load sufficient to induce high magnitude strain (e.g., greater than 1500 microstrain). Such loading not only may not be necessary but also may be detrimental to bone maintenance and well being.

The maintenance of bone mass is commonly believed to be regulated by the peak strain experienced by the bone. Thus, prescribed techniques for mineralization include aggressive exercise or even impact loading, for example, heel drops. For the elderly, these treatment protocols can be difficult to maintain or even dangerous. High loading activity could precipitate the fracture that the exercise was supposed to prevent.

OBJECTS AND SUMMARY OF THE INVENTION

It is an object of the invention to provide apparatus for preventing osteopenia, promoting growth, ingrowth, and healing of bone tissue by a mechanical loading protocol.

It is another object of the invention to provide apparatus for bone tissue growth and maintenance whereby low level strains at physiologically relatively high frequencies are introduced into bone tissue by mechanical loading techniques.

It is yet another object of the invention to provide apparatus for maintaining bone mass and for healing fractures, which apparatus and method utilize mechanical loading of the bone tissue at a relatively low level, high repetition rate or frequency.

It is a further object of the invention to provide apparatus for maintaining bone mass, for accelerating fracture healing and for promoting bone growth and ingrowth by mechanically loading the bone tissue.

It is a specific object of the invention to provide apparatus that is especially applicable to achieving the above objects for bone structure of the human hip and spine.

In accordance with the invention, means for preventing osteopenia, promoting growth, ingrowth, and healing of bone tissue comprises apparatus for applying physiologically based relatively high frequency, relatively low level mechanical load to the bone tissue. The preferred frequency of the mechanical load on the bone tissue is in the range between about 10 and about 50 Hz, and the preferred peak-to-peak level of the mechanical load is sufficient to induce strain on the order of between about 50 and about 500 microstrain. Mechanical loading on bone tissue at strains of this level and induced within the frequency range set forth above can prevent bone loss and enhance new bone formation. Such strains, imparted as transcutaneous loads to a bone, will focus energy at a fracture or bone-deficiency site, by bone transmission via the intervening one or more bone joints or articulations. In the indicated frequency range, the range of microstrain can be accomplished with peak-to-peak vertical displacements less than 2-mm.

Osteopenia, i.e., the loss of bone mass, arises to a large degree from a decrease in muscle activity, such as due to bed rest, cast immobilization, joint reconstruction or old age. This loss can be prevented, or even reversed, if the effect of muscle activity on bone can be mimicked. The inventors have isolated and characterized a relatively high frequency vibration arising from the action of individual muscle cells during contraction, which create mechanical, frequency-specific, low-level oscillations in the subjacent bones. Using in-vivo studies, the inventors have discovered that extremely low-level strains induced into bone within this physiologically based frequency range can prevent bone loss or even enhance new bone formation.

In accordance with the present invention, apparatus is disclosed for implementing a method for preventing osteopenia, and promoting growth, ingrowth and healing of bone tissue, wherein the method comprises the step of inducing a relatively low level, physiologically based, relatively high frequency strain in the bone tissue, by mechanically loading the bone. Fundamental and primary harmonic frequencies induced in the bone by conventional mechanical loading techniques, such as through walking or jogging, are in the range of between 1 and 10 Hz. However, the inventors have discovered that the higher frequency components of such loading, such as caused by muscle vibrations, in the "hyper-physiologic" frequency range of about 10 to about 100 Hz, can have beneficial effects in bone tissue, even when applied at extremely low intensities.

Accordingly, the frequency range of the mechanical strain applied to the bone is preferably between about 10 and about 100 Hz and is more preferably between about 10 and about 50 Hz. The magnitude or peak-to-peak level of the strain induced in the bone tissue is preferably between about 10 and about 1000 microstrain and is more preferably between about 50 and about 500 microstrain at the above-mentioned frequency ranges. The optimal frequency of the mechanical strain is between about 25 Hz and about 35 Hz, and the optimal peak-to-peak level of the load induced in the bone tissue is about 100 microstrain at the optimal frequency range.

The frequency ranges disclosed above are significantly higher than conventional bone treatment protocols while the strain magnitudes are much lower. For example, a program of exercise involving walking or running involves the application of mechanical loading at about 1 or 2 Hz in frequency or repetition rate. Very little energy is transmitted to the bone tissue at the higher level harmonics of this frequency, that is, within the preferred 10 to 50 Hz bandwidth, to stimulate bone-tissue cell activity. As a result, such exercise programs are required to be maintained over an extended period of time. Furthermore, aggressive exercise or even impact loading used as bone-tissue treatment protocols may be difficult to maintain or even dangerous, especially for the elderly. High loading activity could precipitate the fracture that the exercise was supposed to prevent.

The method of the present invention, on the other hand, with its application of lower magnitude mechanical strains at significantly higher frequencies, minimizes the possibility of fracturing or harming the bone tissue, and further minimizes the period of time over which such mechanical loading need be applied. It is believed that about 5 to about 60 minutes per day of exposure to mechanical strains between a frequency of about 10 and about 50 Hz and a load level sufficient to cause between about 50 and about 500 microstrain will induce the appropriate energy into the bone tissue to stimulate the bone-tissue cell activity.

The inventors conducted in vivo experiments on various animals having disuse osteopenia, in which experiments a load sufficient to cause a peak-to-peak strain of 500 microstrain at a frequency of 1 Hz was applied to a control group, and 500 microstrain at a frequency of 15 Hz was induced in another group of animals. The control group exhibited a bone loss of between 10 and 15 percent, which would correspond to a normal 10 percent loss in bone mass normally expected through disuse. On the other hand, the animals experiencing 500 microstrains at a frequency or 15 Hz exhibited an average increase in bone mass of 20 percent, thus reflecting a 30% benefit. Similarly beneficial examples can be given for promotion of bony ingrowth into porous implants and enhancement of fracture healing.

In the embodiments to be described, the invention relies upon an essentially rigid plate of area sufficient to support a patient's body when the spine is upright. This may be accomplished by having the patient stand on the plate or by having the patient sit on the plate. Stiffly compliant means is provided as sole support of the body-loaded plate with reference to a relatively rigid support such as the floor or a chair or bench seat, and one or more dynamic-force transducers beneath the plate are provided to vertically drive the plate with referencing reaction to the relatively rigid support. The spring constant for the compliant means is such that, in the context of the total mass of the plate and of the plate-supported body mass, said total mass and said compliant means exhibit a naturally resonant frequency in the range 10 Hz to 50 Hz.

BRIEF DESCRIPTION OF THE DRAWINGS

Preferred embodiments of the invention will be described in detail, in conjunction with the accompanying drawings, in which:

FIG. 1 is a simplified view, somewhat in perspective, showing a floor-mounted embodiment, accommodating the standing weight of a human body;

FIG. 2 is a perspective view of another embodiment, for chair-mounting, seated accommodation of a human body;

FIG. 3 is a perspective view of a generally cylindrical configuration, representing a further embodiment;

FIG. 4 is a simplified vertical sectional view of the embodiment of FIG. 3;

FIG. 4A is a view similar to FIG. 4 for another embodiment;

FIG. 5 is a view similar to FIG. 4, to show still another embodiment;

FIG. 6 is a simplified view in vertical section to illustrate our presently preferred embodiment;

FIG. 7 is an electrical diagram schematically showing circuitry for operating any of the embodiments of FIGS. 1 to 6;

DETAILED DESCRIPTION OF THE PREFERRED EMBODIMENTS

Figure 8:
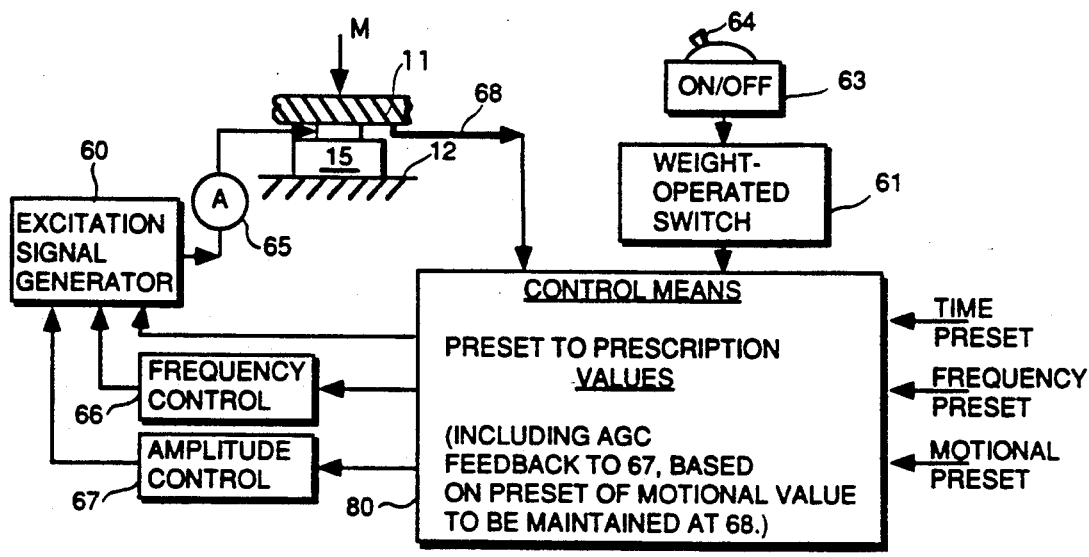
FIG. 8 is a diagram similar to FIG. 7, to show a first modification.

Referring now to the drawings, and in particular to FIG. 1, the invention is shown as a floor-mounted unit 10 comprising spaced upper and lower relatively rigid plates 11, 12, spaced apart by stiffly compliant structure in the form of two oppositely bowed sheets 13, 14, as of spring steel. For the generally rectangular configuration shown, the bowed regions of sheets 13, 14 extend from front to back of unit 10, and this relationship will be understood to apply for the full right-to-left extent of unit 10. The opposite bowing of sheets 13, 14 establishes their vertical separation, to permit mounting of upper and lower end surfaces of one or more vertically linear actuators or transducers 15, 15' along the central vertical plane of symmetry of the bowed regions of sheets 13, 14. Such actuators or transducers may be piezoelectric if small displacements are contemplated, as in the order of 0.05-mm, but for the more general case which contemplates possibly greater displacements, an electromagnetic actuator is presently preferred.

Such electromagnetic actuators are commercially available from different sources, and cylindrically configured moving-coil high-performance linear actuators of BEI Motion Systems Company, Kimco Magnetics Division, San Marcos, Calif., are satisfactory for present purposes, particularly in view of their reliance on a high-energy permanent magnet which, in conjunction with low-mass moving-coil structure, will deliver linear force, without hysteresis, for coil-excitation in the range 10 to 50 Hz, and short-stroke action in ranges as low as 2-mm or less. For better life of wiring, it is preferred to mount the upper or magnetic-core portion of each actuator 15 (15') to the upper one of sheets (13, 14) and the low-mass moving-coil portion of each actuator to the stationary lower sheet (13).

To complete the description of FIG. 1, corner feet 16 provide stable floor reference for plate 12, and relatively soft elastomeric corner spacers 17 between plate 12 and the outer edges of sheet 14 (as well as similar spacers 18 between plate 11 and the outer edges of sheet 13) provide resilient front-to-back stability of plate 11. Such stability is aided by tread markings 19 for correct foot placement on the upper surface of plate 11. And it will be understood that the elastomeric spacers 17, 18 are so softly compliant, in relation to the stiffly compliant nature of sheets 13, 14, that the effect of spacers 17, 18 on the oscillatory action of unit 10, in conjunction with body weight of the user, is negligible.

To implement the purposes and bone-restoring features of the invention, it should be understood that the body of the user is an important physical component.

In the normal gravitational field (1 g), the weight-bearing bones of the appendicular and axial skeleton typically experience, i.e., are subject to, a static strain of about 1000 microstrain. Therefore, any artificial dynamic perturbation of the acceleration of the body will give rise to a corresponding dynamic variation in the strain level experienced by these weight-bearing bones. The magnitude of the strain variation will be in proportion to the ratio of the imposed acceleration, to the acceleration of gravity. Such an artificial acceleration can be imposed by dynamically displacing the body. For example, a 0.01-mm sinusoidal peak-to-peak displacement at 50 Hz will produce a peak body acceleration of 0.1 g, corresponding to an average induced strain of approximately 100 microstrain in the weight-bearing bones.

In FIG. 1, the patient must stand upright, relying upon aligned weight-bearing bones of the feet, legs, hips and spine, as direct links (via associated joints or articulations) to sustain body weight and to permit dynamic mechanical loading, in the course of a given treatment within the preferred frequency range of vertical oscillation. To this end, the stiff compliance of sheets 13, 14 is selected such that, in conjunction with the user's body mass (together with the mass of upper plate 11), a natural resonant frequency in the range 10 to 50 Hz characterizes these factors of stiff compliance and sprung mass. When the user mounts treads 19 on plate 11, he will cause an initial compressing deflection of the bows of sheets 13, 14; but the existence of a naturally resonant relation means that relatively little driving energy is needed from transducers 15, 15' in order to establish the desired amplitude of resonance at the frequency F of natural resonance. Specifically, the naturally resonant frequency F at which this relatively low level of input energy is needed, as the combined output from the transducers 15, 15', follows the relation:

$$F = \sqrt{\frac{k}{M}},$$

where k is the spring constant of sheets 13, 14, and M is the mass, which is essentially the user's body weight, divided by the gravitational constant g. Specifically, at resonance, this low level of input energy is very much smaller than the gravitational force attributable to body weight. And for variants of the described structure wherein, for example, one rather than two (or more) transducers are relied upon to stimulate oscillation, it is the combined level of electrical supply to the moving coil or coils which is involved.

Various other illustrative configurations will be described before describing the circuitry of FIG. 7, which is generally applicable to all of the embodiments of FIGS. 1 to 6.

In FIG. 2, essentially the same body-supporting upper-plate 31 and compliant suspension via bowed stiffly compliant sheets 32, 33 will be recognized from FIG. 1. The essential difference is that in FIG. 2, the lower compliant sheet 33 is mounted directly to a platform 34 which would otherwise be the seat of a chair or stool, having legs 35 for floor reference. Relatively soft corner spacers 36, 36' correspond to spacers 17, 18 of FIG. 1, for stabilizing the orientation of the upper plate 31, which is shown to have a sculptured upper surface contour, for accurately centered adaptability to the user's buttocks. Separate vertical-axis alignments 37, 37' identify the respective central axes of the two force transducers 38, 38' that are relied upon to stimulate oscillation between the bowed portions of the stiffly compliant sheets 32, 33. The considerations involved in operation of the device of FIG. 2 are essentially the same as for FIG. 1, except that the seated body mass of the user (FIG. 2) will have to be accounted as a lesser quantity than the standing mass of the user in FIG. 1, should he relieve his body mass by resting his feet on the floor, while seated on the unit of FIG. 2. But from the aspect of relieving or reversing osteopenia of the spine, the seated arrangement of FIG. 2 can be just as effective as the standing arrangement of FIG. 1 and, at the same time, presumably more comfortable.

FIGS. 3 and 4 illustrate a cylindrical embodiment of the invention, wherein a rigid circular upper plate 40 is stiffly compliantly supported by means schematically suggested as springs 41, which will be understood to be in circumferentially distributed plurality beneath plate 40 and reacting against a rigid lower plate 42 having legs 43 for floor engagement. A central force transducer 44 has a base secured to lower plate 42 and a moving-coil portion engaged to the underside of upper plate. Tread markings or elements 45 on upper plate 40 inform the user of a correct standing position; elements 45 may also incorporate electrical switch action, to be described in connection with FIG. 7, as for initiating and for terminating excitation-voltage supply to the moving coil of transducer 44. An outer shell 46 surrounds the described compliantly suspended structure, with an inward lip which sufficiently overlaps a lower flange of upper plate 40, for purposes of unit-handling retention of described components.

FIG. 4A illustrates a configuration in which the stiffly compliant suspension of the upper-plate member 47 is by way of peripherally distributed pairs of upper and lower springs, which may be stiffly compliant coil springs 48, 48', respectively connected under tensed preload, to frame or housing structure 40 which includes an upper flange formation, for connection to springs 48. A transducer or driver 44' is as described at 44 in FIG. 4.

In the configuration of FIG. 5, external appearance may be generally as depicted in FIG. 3. But the stiffly compliant suspension of a rigid circular upper plate 50 relies upon a radially outward undulation 51 (of circumferential continuity), extending to a peripheral flange portion of mounting to the upper end of the side wall 52 of the lower rigid base plate 53. Once more, a single centered force transducer 54 serves to provide stimulating vertical displacements for effectively tuned operation, involving body mass as an important determinant for natural resonance at a frequency in the desired range.

FIG. 6 is a simplified diagram of our presently preferred configuration which comprises an essentially rigid upper plate 70 spaced from an essentially rigid lower plate 71, wherein the lower plate 71 is part of upstanding frame or housing structure including side walls 72, with an inturned rim flange 73 carried by walls 72 and in lapped register with the periphery of upper plate 70. In the region of the peripheral lap, locating pins 74 carried by upper plate 70 project downwardly for guided loose-fitting location in holes 75 formed in flange 73; snap rings are shown for retaining this loosely located assembly. In the case of a circular configuration as in FIGS. 3 to 5, three such pin-and-hole locating engagements will suffice, but in our presently preferred arrangement, the plates 70, 71 are of generally square configuration, with pins 74 and holes 75 at the four corners. Stiffly compliant support of upper plate 70 is provided by ring-shaped undulating springs, available commercially from Smalley Steel Ring Company, Wheeling, Ill., and it is indicated that a peripheral succession of twelve spaced Smalley "SPIRAWAVE" ring-shaped spring units (Smalley Part No. C175-H1) suffices for a spread of patient body weights ranging from 100 to 200 pounds. Specifically, individual Smalley springs 76 of this type are located by the four corner pins 74, and two further of these springs are retained between rim flange 73 and plate 70 at intervening stretches of the peripheral overlap between flange 73 and plate 70. A single centrally located electromagnetic driver, of nature above described for other embodiments, is shown with its moving-coil assembly 77 secured to lower plate 71, and its outer housing assembly 78 secured to the underside of upper plate 70. Operation is as described for other embodiments, relying on the compliant support and action of all twelve spring units 76.

As indicated above, the drive and control circuitry of FIG. 7 will serve any one of the presently described embodiments. Specifically, such circuitry is shown to comprise signal-generator means 60 for supply of an alternating current to the moving coil of force generator 15, to excite upper plate 11 into natural vertical oscillation with respect to lower plate 12 when gravitationally loaded with a body mass, symbolized at M, it being noted that the stiff compliance of the support (e.g., 13, 14 of FIG. 1) for plate 11 has been so selected for a range of values of M as to exhibit a natural frequency of vertical resonance within the range 10 to 50 Hz. Application of body mass M is operative via switch means 61 to initiate the timing of a treatment interval, e.g., 10 minutes, which has been selected by the setting of timing means 62. As long as the treatment interval is being timed, an ON/OFF switch 63 governing signal generator 60 is connected for the "ON" condition of generator 60, unless either (a) the body mass M is removed from plate 11, or (b) a manually actuable element 64 of switch 63 has been actuated to its "OFF" condition.

In recognition of the fact that different users have different masses which (in the context of a given compliance of plate 11 suspension) will each determine a different natural-resonance frequency in the desired operational range (e.g., 10 to 50 Hz), the circuit of FIG. 7 includes means whereby each individual user may locate the frequency of natural resonance that is unique to him.

Specifically, a motion-indicating sensor 68 (of displacement, velocity or acceleration), carried by the upper plate, may be relied upon to generate a signal indicating the current level of one of these motional quantities, at least for monitoring purposes, whereby amplitude may be adjusted at 67 to the prescribed monitoring level. Generally, it can be observed that peak-to-peak dynamic acceleration should be kept to a level which does not exceed 0.5 g, and that an acceptable range of 50 to 500 microstrain corresponds to peak-to-peak dynamic acceleration values of 0.05 to 0.3 g (corresponding to peak-to-peak displacement in the range 0.1-mm to 2.0-mm), it being preferred to achieve a more limited range of less than 200 microstrain, corresponding to peak-to-peak dynamic acceleration values of less than 0.2 g (corresponding to peak-to-peak displacement values of less than 0.5-mm); more specifically, peak-to-peak displacement is preferably in the range of 0.08-mm to 0.5-mm, corresponding to delivery of bone-tissue strain in the body at a relatively low level of about 100 to 200 microstrain, peak-to-peak. Moreover, it is further preferred that the strain be induced with peak-to-peak displacements no greater than 0.05-mm.

Alternatively, by observing an ammeter 65 that is conveniently within his field of view, while variably adjusting frequency-control means 66 for varying the frequency of the output signal from generator 60 to the moving coil of transducer 15, the user can spot the current anomaly which identifies his compliantly supported frequency of natural resonance; in particular, the current at 65 will be observed to drop, upon attaining the frequency of natural resonance.

If the range of user weight is 2:1, as in the case of user weights ranging between 100 and 200 pounds, the corresponding range of frequencies of natural resonance is $\sqrt{2}$:1, namely, 1.4:1, so that control means 66 will be operative on generator 60 within such a range. But the range 10 to 50 Hz broadly stated above is well beyond 1.4:1, and it is therefore possible to state preference for utilization of a more narrow range of frequencies, such as the range 25 to 35 Hz, or more particularly, the range 15 Hz to 30 Hz. And when it has been better ascertained that and whether an even further restricted range is optimum, it is likely that the fully equipped professional may require a series of selectively replaceable stiffly compliant suspensions 13, 14, having different stiffness coefficients, whereby individual user weights may be more conveniently adapted to narrower bands of naturally resonant frequency. Stated in other words, if the professional is equipped with selectively replaceable stiffly compliant subassemblies, and if it is found that say, the even more restricted frequency range of 29 to 31 Hz is optimum, there is no reason why all persons, regardless of weight, should not be able to avail themselves of the osteogenic benefits achievable through optimum use of the invention.

The apparatus and method of the present invention overcome the inherent disadvantages of conventional mechanical loading, bone treatment protocols. It is less dangerous and more easily applied to the patient, especially the elderly. The lower level of the mechanical strain minimizes the chance of injury to the patient and the bone tissue being treated, and the higher frequency range of the loading significantly reduces the period of time required for such mechanical exposure. Finally, it would appear that bone and connective tissue are acutely responsive to strains induced in the above-mentioned frequency ranges.

It is significant to point out that, inherent in use of the invention, the regions of weakest bone structure are those which are susceptible to greatest induced strain and therefore to the therapeutically beneficial effects attendant such use.

The invention is applicable not only to preventing osteopenia, but also for treatment of fractures by "dynamizing" the fracture, that is, by putting energy into the fracture which causes minute flexing of the bone rather than by keeping the bone rigid, as in the conventional method of bone healing. The invention can also be applied to promote osseointegration, whereby bone need may be encouraged to grow into prosthetic implants or bone grafts.

It is realized that certain users are either incapable (or consider themselves incapable) of following the above-described regimen for uniquely setting the apparatus for the individual's optimum therapy. In such case, it will be understood that currently available techniques of automation exist for totally automatic setting of the device for correct naturally resonant utilization of different individual weights. Several embodiments, specific to different modes of applying the invention, will be described in conjunction with FIGS. 8, and 9, following a general review of principles.

The intent of the apparatus is to permit applied use of the method teachings of our U.S. Pat. Nos. 5,103,806 and 5,191,880. To this end, we have described apparatus to induce mechanical strains on the order of 50 to 500 microstrain (i.e., 50 to 500 times $10^{-6}$ strain) within the frequency range of 10 to 50 Hz, and currently, preferably, within the range of 15 to 30 Hz, into the appendicular and/or axial skeleton.

We have shown that such a treatment protocol can be implemented without resorting to placement of strain gages on the bones of a patient undergoing treatment. This is because we have been able to show that, on average, for a normal healthy adult, a 1-g acceleration (earth's gravitational field) will induce a strain of 1000 microstrain into bone tissue. Therefore, the present intent is that the apparatus shall create a controlled 0.05 to 0.5-g acceleration within the range of 15 to 30 Hz, thus generating 50 to 500 microstrain in the bone.

As a therapeutic device, the most important factor to take into consideration is accurate control of the acceleration/loading, but from a commercial point of view, it is advantageous to be able to implement this method at the lowest possible cost. This can best be accomplished by using the smallest possible electromechanical actuator necessary to create the forces required to attain these accelerations, as the actuator is the most costly component of the apparatus. There are, of course, other advantages to not using brute-force techniques; these include the fact that such non-linear devices are typically difficult to control accurately—they can be noisy, and inefficiencies can lead to undue heating of the device.

To minimize energy input, and therefore tee size of the necessary actuator, we have developed a resonant device which incorporates the mass of the patient as a critical component of the spring-mass system. For proper function, the device and/or the patient must accomplish two tasks:

(1) The driving frequency of the generator must be tuned to the fundamental resonant frequency of the apparatus-patient system. Because each patient's mass will be different, the resonant frequency of the system will be slightly different for each patient, assuming the spring constant of the system is not changed. Specifically, the resonant frequency will vary as the square root of the mass of the patient so that the difference between the resonance frequency for a 100 pound person and a 300 pound person will be approximately 1.73. This difference is sufficient to prevent a small actuator from being able to impose the displacements necessary to achieve the desired accelerations if the system is not tuned to the system resonance; the tuning process is therefore critical.

(2) The amplitude of the driving signal must be adjusted to ensure the correct acceleration of the patient, and correspondingly, the correct strains in the skeleton. The appropriate strain levels to be induced into the skeleton will depend on the condition being treated and are expected to be between 50 and 500 microstrain, i.e., peak accelerations of from 0.05 to 0.5 g. We see at least four distinct clinical situations in which this device will be utilized and which will most likely require different loading protocols:

(a) Maintenance of bone mass/Prevention of osteoporosis—requiring peak accelerations of 0.05 to 0.2 g.

(b) Promotion of bony ingrowth into non-cemented implants—requiring peak accelerations of 0.05 to 0.3 g.

(c) Promotion of bone formation/reversal of osteoporosis—requiring peak accelerations of 0.05 to 0.4 g.

(d) Acceleration of fracture healing—requiring peak accelerations of 0.05 to 0.5 g.

The exact induced strain levels/accelerations will be determined by a physician and will depend on the condition of the patient's bone, the age of the patient, drug treatments the patient may be taking, and the period of time over which the patient will be treated. Nonetheless, once the physician has made a determination, it is incumbent that the device deliver the prescribed treatment, since underloading may not be effective, and overloading may be detrimental.

There are several ways in which an apparatus could accomplish these two critical tasks. However, no device that is commercially available or which, to our knowledge, has been patented appears to be capable of accomplishing them. We envision four variations on the basic apparatus of FIG. 7 which would meet the specifications described above:

(A) A basic unit which is adjusted, prior to delivery to the patient, to operate within the resonant frequency range for a prescribed patient mass and at an amplitude consistent with that prescribed by the physician. Even this basic device, however, will require some automatic gain control (AGC) utilizing feedback from an accelerometer (e.g., output at 68) to compensate for any general wear or tear on the apparatus or for variations in the power-line voltage, etc. Otherwise, one cannot be assured that the patient has experienced the treatment that was prescribed.

(B) A more flexible device which utilizes feedback from both the accelerometer and the driving current (ammeter) to provide the patient with a signal to permit manual adjustment of the resonance condition, and subsequently, the appropriate loading amplitude. Such a device may be necessary for a patient who is undergoing weight loss, who may be using the device with or without a cast, etc. These feedback signals could take the form of an array of lights, a digital readout, an analog meter, an audible sound, etc. The patient could then adjust frequency and amplitude directly through analog or digital input. Note that AGC would still be required for successful implementation of this device.

(C) A refinement of the device of (B) above, to remove the necessity of the patient to monitor the feedback and adjust the frequency and amplitude accordingly. That is, electronic circuitry or software could be developed which will permit the device itself to "hunt" for the resonance condition once the patient stands or sits on the device and turns it on; and then "hunts" for the prescribed amplitude.

(D) A still further refinement of the device would be to make it "smart" by providing the patient with a software key or card that has been encoded with a relevant treatment protocol. In that situation, loading protocols can become quite sophisticated, permitting the amplitude of the loading to vary from day to day during the course of treatment. For example, during treatment of fracture healing, the loading may start out at relatively high levels (0.3 to 0.5 g) and then decrease to lower levels (i.e., a maintenance level of 0.05 to 0.1 g), once the tissue in the fracture callous or implant begins to calcify. Illustratively, the time frame for such a decay would be approximately fifty days. For ingrowth, the decay to "maintenance signal" may take ninety days, and for osteoporosis reversal, the decay may stretch out to two years. The decay could be integral to the smart card, and slope of which could be subject to adjustment by the physician.

The device would need to be able to "read" this encoded protocol and adjust the loading appropriately. Such a device completely removes the necessity of the patient making any setting, and also would permit multiple users in one household to utilize the same device, even if each had a different "prescription" or treatment protocol.

The diagram of FIG. 8 identifies elements of the "basic unit" mentioned above at Item A. Certain components will be recognized from FIG. 7 and have therefore been given the same reference numbers. The additional feature is control means 80 which, by legend, is seen to incorporate means for presetting the apparatus to prescription values of treatment time, as well as the frequency for natural resonance of the combined mass of plate 11 and the patient, it being understood that the physician will have already ascertained, via his own less restricted office apparatus, the patient's frequency of such natural resonance, and he will have preset this value in the apparatus (FIG. 8) which the patient is to use in his own home. Aside from presetting frequency, the apparatus of FIG. 8 includes provision for the physician to enter other prescription data, such as treatment time on the occasion of each use by the patient, and the motional value of output signal to be maintained via automatic-gain control in a feedback-control signal, from the motional signal at 68, to the amplitude-control means 67. For each home treatment, all the patient has to do is to stand or sit on plate 11 (or 31), thus closing the weight-operated switch 61, in readiness for him to manually actuate the on/off switch 63.

The more flexible device of Item B above is perhaps sufficiently illustrated by FIG. 7 wherein the patient can ascertain his own frequency of natural resonance by watching for the dip at ammeter 65 as he varies frequency by adjustment at 66. AGC control of amplitude would be as described at 80 in connection with FIG. 8, but the preset or presettable features of control means 80 would not be needed as long as the patient is willing to follow his physician's instructions. For convenience, the device of Item B can be realized by incorporating the display of ammeter 65 in the control means 80, along with a suitable display of the instantaneous magnitude of motional value, namely, the value of signal output at 68, it being understood that, having set means 66 to the naturally resonant frequency, he should make manual adjustment at 67 to the motional value prescribed for him; thereafter, AGC control, as described, can assure therapeutic benefit from his physician's instructions.

Figure 9:
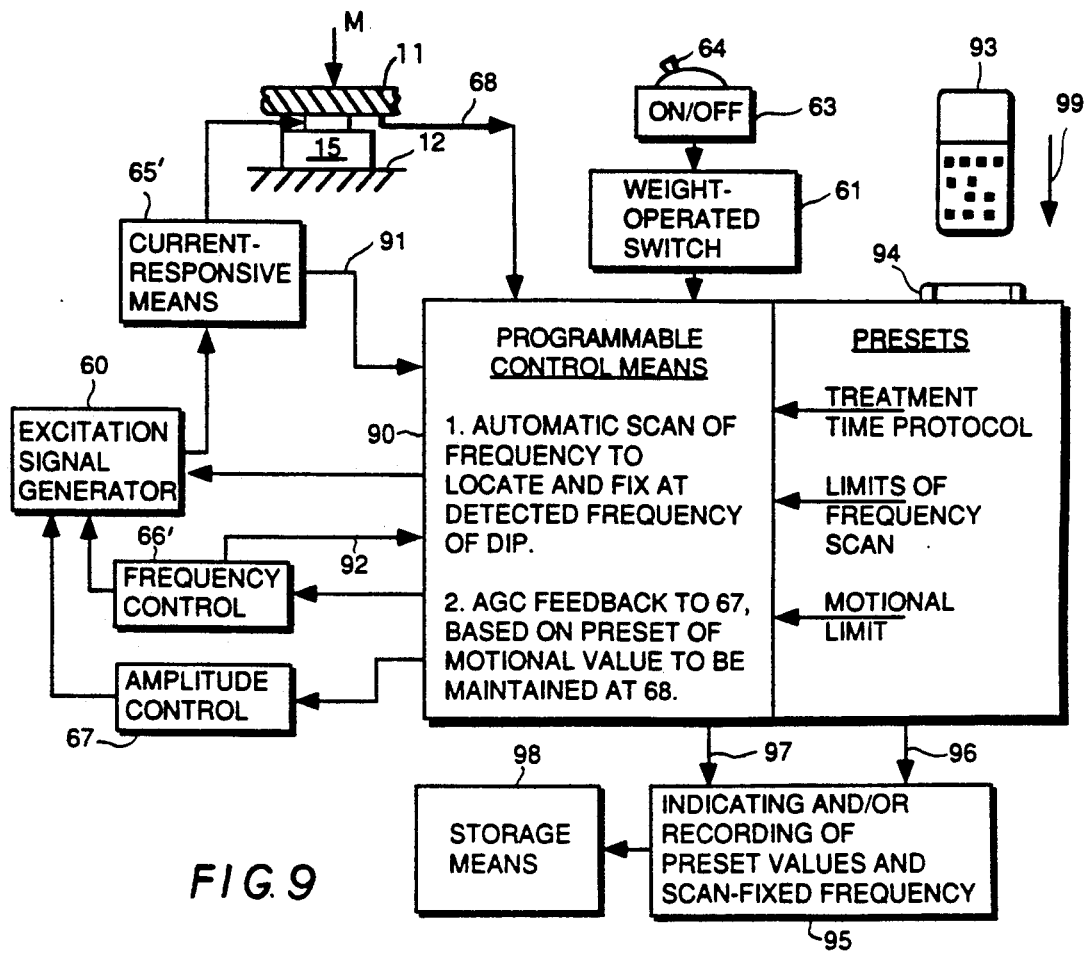
FIG. 9 is also a diagram similar to FIG. 7, to show a second modification.

The diagram of FIG. 9 illustrates components of the "refinement" outlined at Item C above, and again reference numerals repeat, for components already described. The device of FIG. 9 basically incorporates the feature, within programmable control means 90, of automatic scanning control of means 66', to produce a scan of the frequency range of interest, with an ammeter 65' (designated as "current-responsive means") producing an output signal in line 91 to control means 90, whereby the current-signal dip, which identifies the frequency of natural resonance of plate 11 (or 31) plus the patient's body mass, can be identified. Software in control means 90 will be understood also to respond to a frequency-responsive signal in line 92 from means 66' to control means 90, in making this dip-frequency identification, thereby enabling the setting and holding of the thus-identified frequency of natural resonance.

In FIG. 9, presets are as described for FIG. 8, except that, based on the physician's estimate of the probable natural resonance frequency for a particular patient, he may in FIG. 9 present narrower upper and lower limits of the frequency scan, within which limits the naturally resonant frequency for this patient is expected. The device of FIG. 9 is thus fully automatic, in that, once activated by body weight at 61 and manual initiation at 63, the present treatment time or protocol can proceed.

The device of FIG. 9 will be seen to illustrate an office machine for the physician, in that the device enables the physician to let his patient experience a limited exposure to a treatment while the physician is also ascertaining basic data to be preset into the simpler machine of FIG. 8 which the patient is to take home for the patient's simple on/off control of each home treatment.

The device of FIG. 9 will also be understood to indicate an optional feature whereby a patient's regimen in use of the invention can be pursuant to a prescription which is encoded by the physician at his office, as for example by inserting an encoded "smart" card 93 into a loading guide 94 forming part of control means 90. Thus, if the patient leaves the physician's office with his own personalized prescription "smart" card 93, and if a device of FIG. 9 is at his home, then merely by placing his weight on plate 11 (or 31) and inserting his prescription "smart" card in the card guide 94 of his FIG. 9 device, the prescribed treatment can be quickly and automatically set up for the patient's natural resonance. And with subsequent visits to the physician, any further changes in prescription for the same patient can be embodied in a new "smart" card 93 issued to the patient in place of his earlier prescription card.

FIG. 9 will be seen further to illustrate that, in conjunction with suitable digital indicating (or recording) equipment 95, having a direct connection 96 to the presets for control means 90, as well as a direct connection 96 to the control means per se, relevant digital data for the particular patient can be entered into digital storage at 98. Such data are illustratively suggested by legend to include prescription values preset during the patient's visit, as well as data reflecting monitored values of excitation frequency and plate-11 (or 31) motional values. The storage means 98 thus symbolizes means to accumulate a data file on the patient and his progress, and as a data bank, for collation with corresponding data for plural patients undergoing treatment.

Still further, the device of FIG. 9 will be seen to illustrate equipment for the physician wherein, after having ascertained basic data from use on the patient in a given visit, and thus having established or otherwise decided upon preset values unique to a prescription for the patient, the prescription card 93 may be a blank (as to prescription data) but upon insertion into guide 94 and depression to a limit suggested by downward arrow 99, the card stopping at such limit automatically initiates an encoding operation on the card, thereby assuring that the patient will get the newly ascertained prescription protocol on the "smart" card which has just been prepared for him.

What is claimed is:

1. Apparatus for stimulating bone growth in a living vertebrate body of given mass, said apparatus comprising:

upper and lower essentially rigid plates of area sufficient to support the living body when the spine is upright, stiffly compliant means disposed between said plates for vertically compliant coupling of said plates when oriented horizontally for gravitational loading of the upper plate against the lower plate, dynamic-force transducer means interposed between said plates and oriented to vertically drive said upper plate with respect to said lower plate, means associated with said lower plate for retaining an assembled relation of said plates and said compliant means and said transducer means, with freedom for relative displacement of said plates while compliantly coupled, whereby when the lower one of said plates is set upon a horizontal support surface, the upper one of said plates is upwardly facing and positioned for support of a living body with upright spine, said compliant means having a spring constant such that, in the context of the total mass of said upper plate and the plate-supported body mass, said total mass and said compliant means exhibit a naturally resonant frequency in the range 10 Hz to 50 Hz;

variable-frequency signal-generator means for driving said transducer means at said resonant frequency and within a range up to an upper limit of about 2.0-mm displacement peak-to-peak;

signal-generator means including (a) means for varying within said frequency range, the frequency of signal output of said generator means, and (b) means responsive to the instantaneous electric-current value of said signal output, whereby to adjust the varied frequency to a value at which the instantaneous current value is at minimum, said signal-generator means further including amplitude-control means for adjusting the instantaneous amplitude of said signal output; and a motion-indicating sensor carried by said upper plate for indicating the instantaneous motion of said upper plate within said upper limit of displacement peak-to-peak.

2. The apparatus of claim 1, in which said lower plate carries floor engageable means adapted for non-yielding gravitational seating reference to a rigid floor.

3. The apparatus of claim 1, in which said lower plate is mounted to a chair frame.

4. The apparatus of claim 1, in which said stiffly compliant means is an integrally formed peripheral component of said upper plate.

5. Apparatus according to claim 1, further comprising control means for operating said apparatus at said naturally resonant frequency for a per-day limited exposure time in the range of about 5 minutes to about 60 minutes.

6. Apparatus for stimulating bone growth in a vertebrate living body of given mass, said apparatus comprising:

an essentially rigid plate of area sufficient to support the living body when the plate is horizontal and the spine is upright, stiffly compliant means on the underside of said plate for support of said plate upon a relatively rigid horizontal support surface, dynamic-force transducer means carried by the underside of said plate and oriented to vertically drive said plate with referencing reaction to the relatively rigid support surface, said compliant means having a spring constant such that, in the context of the total of the mass of said plate and the mass of the plate-supported body mass, said total mass and said compliant means exhibit a naturally resonant frequency in the range 10 Hz to 50 Hz, variable-frequency signal-generator means for driving said transducer means at said resonant frequency and within a range up to an upper limit of about 2.0-mm displacement peak-to-peak;

said signal-generator means including (a) means for varying, within said frequency range, the frequency of signal output of said generator means, and (b) means responsive to the instantaneous electric-current value of said signal output, whereby to adjust the varied frequency to a value at which the instantaneous current value is at minimum, said signal-generator means further including amplitude-control means for adjusting the instantaneous amplitude of said signal output; and a motion-indicating sensor carried by said plate for indicating the instantaneous motion of said plate within said upper limit of displacement peak-to-peak.

7. The apparatus of claim 6, in which said stiffly compliant means has an upper end connected to said plate and a lower end adapted for gravitational seating reference to a rigid floor.

8. The apparatus of claim 6, in which said stiffly compliant means has an upper end connected to said plate and a lower end adapted for non-yielding gravitational seating reference to a chair frame.

9. The apparatus of claim 6, in which said stiffly compliant means is an integrally formed peripheral component of said plate and in which the periphery of said peripheral component is the sole means of plate support.

10. Apparatus according to claim 1 of claim 6, in which said resonant frequency is in the range 25 Hz to 35 Hz.

11. Apparatus according to claim 1 or claim 6, in which said peak-to-peak displacement is in the range 0.01 mm to 2.0 mm, corresponding to delivery of bone-tissue strain in the body at a relatively low level of about 50 to about 500 microstrain, peak-to-peak.

12. Apparatus according to claim 1 or claim 6, in which said peak-to-peak displacement is in the range 0.08 mm to 0.5 mm, corresponding to delivery of bone-tissue strain in the body at a relatively low level of about 100 to about 200 microstrain, peak-to-peak.

13. Apparatus according to claim 1 or claim 6, in which said peak-to-peak displacement is no greater than 0.05 mm.

14. The apparatus of claim 1 or claim 6, in which said transducer means is a linear electromagnetic actuator.

15. The apparatus of claim 1 or claim 6, in which said transducer means is a piezoelectric actuator.

16. The apparatus of claim 1 or claim 6, wherein said means for driving said transducer is activated by switch means responsive to compressive displacement of said stiffly compliant means upon application of living body weight to said apparatus.

17. The apparatus of claim 1 or claim 6, wherein said means for driving said transducer is activated by switch means responsive to compressive displacement of said stiffly compliant means upon application of living body weight to said apparatus, and interval-timing means associated with said transducer-driving means for disconnecting the drive of said transducer means upon timing-out a predetermined interval of body-loaded transducer operation.

18. Apparatus according to claim 6, in which said stiffly compliant means is the sole means of support of said plate.

19. Apparatus according to claim 6, in which said stiffly compliant means is mounted to floor-engageable means adapted for non-yielding gravitational seating reference to a rigid floor.

20. Apparatus according to claim 6, in which said stiffly compliant means is mounted to a bench seat.

21. Apparatus according to claim 6, and control means for operating said apparatus at said naturally resonant frequency for a per-day limited exposure time in the range of about 5 minutes to about 60 minutes.

22. Apparatus for stimulating bone growth in a vertebrate living body of given mass, said apparatus comprising:
   an essentially rigid upper plate of area sufficient to support the living body when the spine is upright,
   a rigid lower plate forming part of a rigid frame structure which includes a peripheral rim above at least a portion of said upper plate, with said upper plate exposed within said rim for support of the living body,
   stiffly compliant means in the form of peripherally distributed pairs of upper and lower springs under tensed preload, the upper springs being connected to said upper plate and to said rim, and the lower springs being connected to said upper plate and to said lower plate whereby said upper plate is suspended with respect to said frame structure by all said springs under tensed preload,
   dynamic-force transducer means interposed between said plates and oriented to vertically drive said upper plate with respect to said lower plate;
   said compliant means having a spring constant such that, in the context of the total mass of said upper plate and the plate-supported body mass, said total mass and said compliant means exhibit a naturally resonant frequency in the range 10 Hz to 50 Hz,
   variable-frequency signal-generator means for driving said transducer means at said resonant frequency and within a range up to an upper limit of about 2.0-mm displacement peak-to-peak;
   said signal-generator means including
      (a) means for varying, within said frequency range, the frequency of signal output of said generator means, and
      (b) means responsive to the instantaneous electric-current value of said signal output, whereby to adjust the varied frequency to a value at which the instantaneous current value is at minimum,
   said signal-generator means further including amplitude-control means for adjusting the instantaneous amplitude of said signal output; and
   a motion-indicating sensor carried by said plate for indicating the instantaneous motion of said plate within said upper limit of displacement peak-to-peak.

23. The apparatus of claim 1 or claim 22 in which said stiffly compliant means is a peripheral rim of said upper plate having peripheral contact with said lower plate and providing the sole means of upper-plate support.

24. Apparatus for stimulating bone growth in a living vertebrate body of given mass, said apparatus comprising:
   upper and lower essentially rigid plates of area sufficient to support the living body when the spine is upright,
   stiffly compliant means disposed between said plates for vertically compliant coupling of said plates when oriented horizontally for gravitational loading of said upper plate against said lower plate,
   dynamic-force transducer means interposed between said plates and oriented to vertically drive said upper plate with respect to said lower plate;
   means associated with said lower plate for retaining an assembled relation of said plates and said compliant means and said transducer means, with freedom for relative displacement of said plates while compliantly coupled,
   whereby when the lower one of said plates is set upon a horizontal support surface the upper one of said plates is upwardly facing and positioned for support of a living body with upright spine,
   said compliant means having a spring constant such that, in the context of the total mass of said upper plate and the plate-supported body mass, said total mass and said compliant means exhibit a naturally resonant frequency in the range 10 Hz to 50 Hz,
   means for driving said transducer means at said resonant frequency and within a range up to 2.0-mm displacement peak-to-peak;
   said means for driving said transducer means being an alternating-current signal generator with means for selectively varying the output frequency within said range of naturally resonant frequencies; and
   means for monitoring an instantaneous motional value of said upper plate at natural resonance and in the course of frequency variation, whereby to establish the natural resonance for an applied individual's body mass.

25. Apparatus for stimulating bone growth in a living vertebrate body of given mass, said apparatus comprising:
   upper and lower essentially rigid plates of area sufficient to support the living body when the spine is upright, stiffly compliant means disposed between said plates for vertically compliant coupling of said plates when oriented horizontally for gravitational loading of said upper plate against said lower plate, dynamic-force transducer means interposed between said plates and oriented to vertically drive said upper plate with respect to said lower plate;

means associated with said lower plate for retaining an assembled relation of said plates and said compliant means and said transducer means, with freedom for relative displacement of said plates while compliantly coupled, whereby when the lower one of said plates is set upon a horizontal support surface the upper one of said plates is upwardly facing and positioned for support of a living body with upright spine, said compliant means having a spring constant such that, in the context of the total mass of said upper plate and the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating-current signal generator with means for selectively varying the magnitude of output current to said transducer means; and means carried by said upper plate for monitoring a quantity reflecting an instantaneous motional value of said upper plate at natural resonance, whereby to enable selective adjustment of the magnitude of current supplied to said transducer means, to or within a predetermined monitored limit.

26. Apparatus for stimulating bone growth in a living vertebrate body of given mass, said apparatus comprising:

upper and lower essentially rigid plates of area sufficient to support the living body when the spine is upright, stiffly compliant means disposed between said plates for vertically compliant coupling of said plates when oriented horizontally for gravitational loading of said upper plate against said lower plate, dynamic-force transducer means interposed between said plates and oriented to vertically drive said upper plate with respect to said lower plate;

means associated with said lower plate for retaining an assembled relation of said plates and said compliant means and said transducer means, with freedom for relative displacement of said plates while compliantly coupled, whereby when the lower one of said plates is set upon a horizontal support surface the upper one of said plates is upwardly facing and positioned for support of a living body with upright spine, said compliant means having a spring constant such that, in the context of the total mass of said upper plate and the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating current signal generator with means for selectively varying the magnitude of output current to said transducer means; and accelerometer means carried by said upper plate for monitoring the instantaneous value of a maximum dynamic acceleration of said upper plate at said natural resonance so as to assure control of output current to an upper limit corresponding to a maximum monitored dynamic acceleration value of 0.3 g.

27. Apparatus for stimulating bone growth in a living vertebrate body of given mass, said apparatus comprising:

upper and lower essentially rigid plates of area sufficient to support the living body when the spine is upright, stiffly compliant means disposed between said plates for vertically compliant coupling of said plates when oriented horizontally for gravitational loading of said upper plate against said lower plate, dynamic-force transducer means interposed between said plates and oriented to vertically drive said upper plate with respect to said lower plate;

means associated with said lower plate for retaining an assembled relation of said plates and said compliant means and said transducer means, with freedom for relative displacement of said plates while compliantly coupled, whereby when the lower one of said plates is set upon a horizontal support surface the upper one of said plates is upwardly facing and positioned for support of a living body with upright spine, said compliant means having a spring constant such that, in the context of the total mass of said upper plates and the plate-supported body mass, said total mass and said compliant means exhibit a naturally resonant frequency in the range 10 Hz to 50 Hz;

means for driving said transducer means at said resonant frequency and within a range up to 2.0-mm displacement peak-to-peak;

said means for driving said transducer means being an alternating current signal generator with means for selectively varying the magnitude of output current to said transducer means; and displacement-responsive monitoring means carried by said upper plate for monitoring the instantaneous value of peak-to-peak displacement of said upper plate at said natural resonance so as to assure control of output current to an upper limit corresponding to a maximum monitored peak-to-peak displacement of 2.0 mm.

28. Apparatus for stimulating bone growth in a living vertebrate body of a given mass, said apparatus comprising:

an essentially rigid plate of area sufficient to support the living body when the plate is horizontal and the spine is upright, means for supporting said plate including stiffly compliant means engaged to said plate, dynamic-force transducer means engaged to the underside of said plate and oriented to vertically drive said plate with referencing reaction to a relatively rigid support surface, said compliant means having a spring constant such that, in the context of the total of the mass of said plate and the mass of the plate-supported body mass, said total mass and said compliant means exhibit a naturally resonant frequency in the range 10 Hz to 100 Hz, and variable-frequency signal-generator means for driving said transducer means at said resonant frequency and within a range up to an upper limit of about 2.0-mm displacement peak-to-peak;

said signal-generator means including (a) means for varying, within said frequency range, the frequency of signal output of said generator means, and (b) means responsive to the instantaneous electric-current value of said signal output, whereby to adjust the varied frequency to a value at which the instantaneous current value is at minimum, said signal-generator means further including amplitude-control means for adjusting the instantaneous amplitude of said signal output; and a motion-indicating sensor carried by said plate for indicating the instantaneous motion of said plate within said upper limit of displacement peak-to-peak.

29. Apparatus according to claim 28, in which said stiffly compliant means is peripherally engaged to said plate.

30. Apparatus according to claim 28, in which said stiffly compliant means is engaged to the underside of said plate.

31. Apparatus according to claim 28, further comprising control means for operating said apparatus at the frequency of thus-established natural resonance for a per-day limited exposure time in the range of about 5 minutes to about 60 minutes.

32. Apparatus for stimulating bone growth in a vertebrate living body of given mass, said apparatus comprising:

an essentially rigid plate of area sufficient to support the living body when the plate is horizontal and the spine is upright, stiffly compliant means on the underside of said plate for support of said plate upon a relatively rigid horizontal support surface, dynamic-force transducer means carried by the underside of said plate and oriented to vertically drive said plate with referencing reaction to the relatively rigid support surface, said compliant means having a spring constant such that, in the context of the total of the mass of said plate and the mass of the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating-current signal generator with means for selectively varying the output frequency within said range of naturally resonant frequencies; and means for monitoring an instantaneous motional value of said upper plate at natural resonance and in the course of frequency variation, whereby to establish the natural resonance for an applied individual's body mass.

33. Apparatus for stimulating bone growth in a vertebrate living body of given mass, said apparatus comprising:

an essentially rigid plate of area sufficient to support the living body when the plate is horizontal and the spine is upright, stiffly compliant means on the underside of said plate for support of said plate upon a relatively rigid horizontal support surface, dynamic-force transducer means carried by the underside of said plate and oriented to vertically drive said plate with referencing reaction to the relatively rigid support surface, said compliant means having a spring constant such that, in the context of the total of the mass of said plate and the mass of the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating current signal generator with means for selectively varying the magnitude of output current to said transducer means; and means carried by said plate for monitoring a quantity reflecting an instantaneous motional value of said plate at natural resonance, whereby to enable selective adjustment of the magnitude of current supplied to said transducer means to or within a predetermined monitored limit.

34. Apparatus for stimulating bone growth in a vertebrate living body of given mass, said apparatus comprising:

an essentially rigid plate of area sufficient to support the living body when the plate is horizontal and the spine is upright, stiffly compliant means on the underside of said plate for support of said plate upon a relatively rigid horizontal support surface, dynamic-force transducer means carried by the underside of said plate and oriented to vertically drive said plate with referencing reaction to the relatively rigid support surface, said compliant means having a spring constant such that, in the context of the total of the mass of said plate and the mass of the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating-current signal generator with means for selectively varying the magnitude of output current to said transducer means; and accelerometer means carried by said upper plate for monitoring the instantaneous value of a maximum dynamic acceleration of said upper plate at said natural resonance so as to assure control of output current to an upper limit corresponding to a maximum monitored dynamic acceleration value of 0.3 g.

35. Apparatus for stimulating bone growth in a vertebrate living body of given mass, said apparatus comprising:

an essentially rigid plate of area sufficient to support the living body when the plate is horizontal and the spine is upright, stiffly compliant means on the underside of said plate for support of said plate upon a relatively rigid horizontal support surface, dynamic-force transducer means carried by the underside of said plate and oriented to vertically drive said plate with referencing reaction to the relatively rigid support surface, said compliant means having a spring constant such that, in the context of the total of the mass of said plate and the mass of the plate-supported body mass, said total mass and said compliant means exhibit a naturally resonant frequency in the range 10 Hz to 50 Hz, means for driving said transducer means at said resonant frequency and within a range up to 2.0-mm displacement peak-to-peak;

said means for driving said transducer means being an alternating-current signal generator with means for selectively varying the magnitude of output current to said transducer means, and displacement-responsive monitoring means carried by said plate for monitoring the instantaneous value of peak-to-peak displacement of said plate at said natural resonance so as to assure control of output current to an upper limit corresponding to a maximum monitored peak-to-peak displacement of 2.0 mm.

36. Apparatus for stimulating bone growth in a living vertebrate body of a given mass, said apparatus comprising:

an essentially rigid plate of area sufficient to support the living body when the plate is horizontal and the spine is upright, means for supporting said plate including stiffly compliant means engaged to said plate, dynamic-force transducer means engaged to the underside of said plate and oriented to vertically drive said plate with referencing reaction to a relatively rigid support surface, said compliant means having a spring constant such that, in the context of the total of the mass of said plate and the mass of the plate-supported body mass, said total mass and said compliant means exhibit a naturally resonant frequency in the range of 10 Hz to 100 Hz, variable-frequency signal-generator means connected to drive said transducer means at said resonant frequency and within a range up to an upper limit of about 2.0-mm displacement peak-to-peak;

presettable means for setting the frequency output of said signal-generating means to a preascertained value of said naturally resonant frequency, a motion-indicating sensor carried by said plate for providing an electrical-signal output that reflects instantaneous motion of said plate within said upper limit of displacement peak-to-peak, and feedback-control means responsive to said electrical-signal output and having an amplitude-control connection to said signal-generator means.

37. Apparatus according to claim 36, in which presettable means associated with said amplitude-control connection is operative to selectively limit the amplitude of excitation to said signal generating means for selective limitation of plate motion to a predetermined value less than said upper limit of displacement peak-to-peak.

38. Apparatus according to claim 36, further comprising control means for operating said apparatus to treat the body at the preascertained value of said naturally resonant frequency for a per-day exposure period of time in the range of about 5 minutes to about 60 minutes, wherein the body exposure is to mechanical strains in the range between about 50 and about 500 microstrain.

39. Apparatus for stimulating bone growth in a living vertebrate body of given mass, said apparatus comprising:

an essentially rigid plate of area sufficient to support the living body when the plate is horizontal and the spine is upright, means for supporting said plate including stiffly compliant means engaged to said plate, dynamic-force transducer means engaged to the underside of said plate and oriented to vertically drive said plate with referencing reaction to a relatively rigid support surface, said compliant means having a spring constant such that, in the context of the total of the mass of said plate and the mass of the plate-supported body mass, said total mass and said compliant means exhibit a naturally resonant frequency in the range 10 Hz to 100 Hz, variable-frequency signal-generator means for driving said transducer means at said resonant frequency and within a range up to an upper limit of about 2.0-mm displacement peak-to-peak; and automatic means for ascertaining said naturally resonant frequency, comprising:

scanning means for varying the frequency output of said signal-generator means within said range of frequencies, and means responsive to instantaneous current supplied by said generator means to said transducer means in a course of frequency variation, for identifying a frequency at which instantaneous current is at minimum value within said range of frequencies.

40. Apparatus according to claim 39, wherein said automatic means includes means setting the frequency of said signal-generator means to the thus-identified frequency, a motion-indicating sensor carried by said plate for providing an electrical-signal output that reflects instantaneous motion of said plate, and amplitude-control means for said signal-generator means and responsive to said electrical-signal output for regulating instantaneous plate motion to a predetermined level which is less than said upper limit of displacement peak-to-peak.

41. Apparatus according to claim 40, in which said predetermined level of amplitude control is a variable level which decreases to a predetermined minimum maintenance level in a course of treatment time.

42. Apparatus according to claim 39, in which said naturally resonant frequency is in the range 10 Hz to 50 Hz.

43. Apparatus according to claim 39, further comprising control means for operating said apparatus to treat the body at said ascertained naturally resonant frequency for a per-day exposure period of time in the range of about 5 minutes to about 60 minutes, wherein the body exposure is to mechanical strains in the range between about 50 and about 500 microstrain.

44. Apparatus for stimulating bone growth in a living vertebrate body of a given mass, said apparatus comprising:

an essentially rigid plate of area sufficient to support the living body when the plate is horizontal and the spine is upright, means for supporting said plate including stiffly compliant means engaged to said plate, dynamic-force transducer means engaged to the underside of said plate and oriented to vertically drive said plate with referencing reaction to a relatively rigid support surface, said compliant means having a spring constant such that, in the context of the total of the mass of said plate and the mass of the plate-supported body mass, said total mass and said compliant means exhibit a naturally resonant frequency in the range 10 Hz to 100 Hz, variable-frequency signal-generator means for driving said transducer means at said resonant frequency and within a range up to an upper limit of about 2.0-mm displacement peak-to-peak; and control means for said signal-generator means including:

(a) means for varying, within said frequency range, the frequency of signal output of said generator means, (b) means responsive to the instantaneous electric-current value of said signal output, whereby to adjust the varied frequency to a value at which the instantaneous current value is at minimum, (c) amplitude-control means for adjusting the instantaneous amplitude of said signal output, and (d) feedback-control means including a motion-indicating sensor carried by said plate for producing an electrical signal indicative of said instantaneous motion, and said sensor being connected to said amplitude-control means for maintaining a predetermined level of sensor output in the course of a given treatment.

45. Apparatus according to claim 44, in which said control means includes means for pre-setting treatment time.

46. Apparatus according to claim 44, in which said control means includes means for pre-setting a predetermined output level of said sensor.

47. Apparatus according to claim 44, in which said control means includes means for presetting signal-generator output frequency to a fixed value which has been predetermined to be the correct resonance frequency for a patient using the apparatus.

48. Apparatus according to claim 44 in which said control means includes a microprocessor having means programmed to perform a frequency scan for minimum current to said transducer and to identify the frequency at which said minimum current is found to occur, and then to establish the identified frequency as the fixed frequency of signal-generator output to said transducer.

49. Apparatus according to claim 48, in which the programming of said microprocessor includes means for presetting limits of said frequency scan to values which are at relatively close proximity but are spaced on opposite sides of a pre-established value of said fixed frequency, said pre-established value being from a prior use of said apparatus for the same patient.

50. Apparatus according to claim 48, in which the means programmed to perform a frequency scan includes a prescription-encoded member that is unique to a particular patient's requirements.

51. Apparatus according to claim 48, in which said microprocessor is connected for continuous response to said sensor and for providing automatic-gain control to maintain such amplitude control of signal-generator output as to retain sensor output at substantially a predetermined treatment level.

52. Apparatus according to claim 48, in which said control means includes means for displaying or recording preset data and measured motional-output data, and in which the said microprocessor includes means for automatic entry of said data into a display or a recording.

53. Apparatus according to claim 48, in which said control means is associated with a digital-storage device, and in which said microprocessor includes means for automatic entry of preset data and of measured motional-output data into digital storage.

54. Apparatus according to claim 44, in which said control means is operative to maintain said predetermined level of sensor output for a per-day exposure period of treatment time in the range between about 5 minutes to about 60 minutes.

* * * * *